United States Patent [19]

Blanc et al.

[11] Patent Number: 4,935,043
[45] Date of Patent: Jun. 19, 1990

[54] CRYOGENIC PROCESS FOR DESULPHURIZATION AND GASOLINE REMOVAL OF A GASEOUS MIXTURE COMPRISING METHANE CONTAINING $H_2S$ AND HYDROCARBONS HAVING 2 CARBON ATOMS AND HIGHER

[75] Inventors: Claude Blanc, Pau; Henri Paradowski, Cergy, both of France

[73] Assignee: Societe Nationale Elf Aquitaine (Production), Paris, France

[21] Appl. No.: 309,796
[22] PCT Filed: May 10, 1988
[86] PCT No.: PCT/FR88/00227
§ 371 Date: Feb. 21, 1989
§ 102(e) Date: Feb. 21, 1989
[87] PCT Pub. No.: WO88/08833
PCT Pub. Date: Nov. 17, 1988

[30] Foreign Application Priority Data

May 15, 1987 [FR] France .................................. 8706843

[51] Int. Cl.[5] .................................................. F25J 3/00
[52] U.S. Cl. ............................................. 62/20; 62/24
[58] Field of Search ............................. 62/17, 20, 24

[56] References Cited

U.S. PATENT DOCUMENTS

| | | | |
|---|---|---|---|
| 4,488,890 | 12/1984 | Foerg et al. | 62/20 |
| 4,556,404 | 12/1985 | Shenoy et al. | 62/20 |
| 4,563,202 | 1/1986 | Yao et al. | 62/20 |
| 4,707,171 | 11/1987 | Bauer | 62/20 |
| 4,710,211 | 12/1987 | Gazzi et al. | 62/20 |
| 4,713,940 | 12/1987 | Ranke et al. | 62/20 |
| 4,740,222 | 4/1988 | Mehra et al. | 62/20 |

Primary Examiner—Ronald C. Caposselo
Attorney, Agent, or Firm—Burgess, Ryan and Wayne

[57] ABSTRACT

A cryogenic process of simultaneous selective desulphurization and gasoline removal of a gaseous mixture consisting mainly of methane and likewise containing $H_2S$ and hydrocarbons with $C_2$ and more.

Said gaseous mixture (1), after having eventually undergone an operation of removal of benzol (25) and then cooling (2) producing condensates (4), is washed between 0° C. and −45° C. by means of a solvent (5) selective of $H_2S$ to produce a current of methane (64) having a partial pressure in $H_2S$ below 65 Pa and a liquid phase (9a) rich in $H_2S$ and containing at least 80% molar of the hydrocarbons of $C_3$ and more of the gaseous mixture (1). The liquid phase (9a) is subjected to a demethanization (29, 9) producing a demethanized rich solvent (11) and a gaseous phase rich in methane (10), the solvent (11) then is cooled between −25° and −80° C. sufficiently to produce its dissociation in a lower liquid fraction (38) that contains the $H_2S$ and, in methane equivalent, less than 5% molar of hydrocarbons and an upper liquid fraction (37) formed of the hydrocarbons of $C_3$ and more. Said fractions (37, 38) are separated and the fraction (38) undergoes a regeneration (46, 16, 20) to produce a current (24) of acid gas rich in $H_2S$ and containing the small amount cited above of hydrocarbons and a regenerated solvent (21).

20 Claims, 4 Drawing Sheets

CRYOGENIC PROCESS FOR DESULPHURIZATION AND GASOLINE REMOVAL OF A GASEOUS MIXTURE COMPRISING METHANE CONTAINING $H_2S$ AND HYDROCARBONS HAVING 2 CARBON ATOMS AND HIGHER

BACKGROUND OF THE INVENTION

The invention concerns a cryogenic process of simultaneous selective desulphuration and gasoline removal of a gaseous mixture consisting mainly of methane and likewise containing $H_2S$, hydrocarbons with $C_2$ and more, and eventually one or more gaseous compounds selected among the inert gases $H_2O$, $CO_2$, COS and mercaptans, said gaseous mixture being under an absolute pressure above 0.5 MPa. The process according to the invention makes it possible directly to separate a gaseous mixture of the above mentioned type in three components, namely:
- a treated gas mainly consisting of methane in which the partial pressure $H_2S$ is less than 65 Pa and the total partial pressure of sulphur-containing compounds, when the gaseous mixture to be treated contains COS and/or mercaptans in addition to $H_2S$, is less than 260 Pa,
- one fraction of heavy hydrocarbons containing at least 80% molar of hydrocarbons of $C_3$ and more present in the gaseous mixture to be treated, and
- one stream of acid gas consisting of $H_2S$ eventually mixed with a more or less considerable quantity of acid compounds $CO_2$, COS and mercaptans, when said compounds are present in the gaseous mixture to be treated, said stream of acid gas containing, one the one hand, less than 5% molar of hydrocarbons expressed in methane equivalent in relation to the $H_2S$ and other acid compounds and more than 80% of the $H_2S$ contained in the gaseous mixture to be treated, and, on the other hand, having a molar ratio $H_2S:CO_2$ higher than the ratio that corresponds in the gaseous mixtures to be treated.

STATEMENT OF RELATED ART

There are known several processes industrially used for the treatment of gaseous mixtures such as defined above, the main examples of them being represented by the different natural gases which include an operation of deacidification, that is, an elimination of the $H_2S$ and other acid gases, and an operation of gasoline removal, that is, a separation of the heavy hydrocarbons, for example, of $C_3$ and more, from the gaseous mixture, which make it possible to carry out the separation of said gaseous mixture into the three components mentioned above. Said operations of deacidification and gasoline removal are generally carried out separately and form part of a succession of operations effected on the gaseous mixture to be treated and mainly including an elimination of the acid gases, drying, an adsorption of water on a suitable solid material such as a molecular sieve, a separation by cryogenic distillation between $-30°$ C. and $-90°$ C. associated or not with an extraction by a solvent in order to obtain the fraction of liquid of natural gas, and finally a reheating of the treated gas to room temperature in order, generally, to feed the network of commercial gas.

In such a diagram of treatment of a gaseous mixture of the natural gas type containing the above mentioned constituents, the lowering of the temperature of the gaseous mixture is imposed only by the production of the fraction of natural gas, no other operation being effected at this level of temperature.

In this type of treatment diagram, the performance in series of operations which are based on very different principles and are conducted at different levels of temperature involves serious inconveniences. There is only scant possibility of thermal integration, which makes said diagram of treatment extremely burdensome from the point of view of energy and from the point of view of investments. Besides, at the level of the stage of elimination of the acid gaseous compounds, which generally constitutes the first stage of said diagram of treatment, and usually consists in washing the gaseous mixture to be treated, in counter-current, by means of a solvent of acid gaseous compounds, selective or not of the $H_2S$, and regeneratable as an aqueous solution of an alkanolamine or of potassium carbonate, or even an organic solvent, restraints appear in the selection of the solvent from the moment the gaseous mixture to be treated contains quantities, even if quite small, of hydrocarbons having $C_3$ or more.

In effect, the industrially available organic solvents susceptible of efficiently dissolving $H_2S$ and the other acid compounds such as $CO_2$, COS and mercaptans such as propylene carbonate, methanol, N-methylpyrrolidone, dimethyl ether of ethylene glycol or of polyethylene glycols having from $C_4$ to $C_{12}$ can only be used if the gaseous mixture to be treated contains only very small quantities of said hydrocarbons. Otherwise these hydrocarbons having $C_3$ and more are largely absorbed by the organic solvent and are found again in the stream of acid gas containing $H_2S$ produced in the course of the regeneration of the solvent, which has as consequence, when said stream of acid gas is habitually used in a sulphur plant, a deficient operation of the latter, and it is then preferable to discard the use of organic solvents in favor of solvents consisting of aqueous solutions of amines, specially alkanolamines, or of potassium carbonate.

There are known also processes for treatment of gaseous mixture of the type of natural gases which make it possible simultaneously to carry out the elimination of the acid gases contained in the gaseous mixture and the production of gaseous hydrocarbons and of liquid hydrocarbons, the typical of said processes being the one known by the name of RYAN-HOLMES process, specially described by J. RYAN and F. the review CHEMICAL ENGINEERING PROGRESS, October 1984, pages 53 to 56. In such a process the natural gas to be treated, after having been dehydrated in a conventional manner and then refrigerated, is subjected to a distillation at low temperature carried out in three or four successive stages. In the method in three stages, the dehydrated and refrigerated natural gas is separated in a first column (demethanizer) at the top of which is injected an additive consisting of a liquid fraction of hydrocarbons of $C_4$ and more in a gaseous phase containing the methane and the lighter compounds and a liquid fraction containing the hydrocarbons of $C_2$ and more and the acid gases. Said liquid fraction is separated in a second column (de-ethanizer) in which there is likewise introduced a certain quantity of the additive in a head fraction consisting of $CO_2$ and in a tail fraction containing the hydrocarbons of $C_2$ and more and the $H_2S$. Said tail fraction is then separated, in a third column, in a head fraction consisting of a liquid fraction of hydrocarbons of from $C_2$ to $C_4$ containing $H_2S$ and a tail fraction consisting of a liquid fraction of hydrocarbons of $C_4$ and more, which contains most of the butanes and higher hydrocarbons present in the treated natural gas and from which the adequate quantity is removed for constituting the additive injected in the first and second columns. The use of said additive prevents the crystallization of $CO_2$ at the top of the demethanizer and ensures the rupture of the azeotrope that forms between the ethane and $CO_2$ and facilitates the separation of these compounds in the de-ethanizer. The liquid fraction of hydrocarbons of from $C_2$ to $C_4$ containing the $H_2S$ is then subjected to washing by means of an aqueous amine solution for furnishing a purified liquid fraction of hydrocarbons of from $C_2$ to $C_4$ and a stream of acid gas containing $H_2S$ and eventually $CO_2$ which can be used for the production of sulphur in the CLAUS units.

In such a process the need of having recourse to an additive, on one hand, for preventing the crystallization of the $CO_2$ at the top of the demethanizer and, on the other hand, for breaking the azeotrope between the ethane and $CO_2$ in the de-ethanizer makes more complicated the carrying out of the process and for this reason more burdensome.

It is also known that the acid gases, specially $H_2S$ contained in a natural gas, can be eliminated by washing with a solvent such as methanol by operating at temperatures generally below $-10°$ C. Particularly in the citation FR-A-2550956 there is proposed a process of this type in which the natural gas is washed by cold methanol by operating in a plurality of washing zones serially disposed and the temperature of operation of which preferably decreases from one zone to the zone immediately below. The natural gas to be treated, which has been injected at the entrance of the first zone, passes from one zone to the one that follows to exit from the last zone greatly impoverished in acid gases while cold methanol is injected in each zone and separated from the natural gas at the exit from this zone. The methanol introduced in each zone other than the last one is the used methanol separated at the exit of the zone immediately below while the methanol separated from the first zone serves, after regeneration, to feed the last zone. Before the phase of washing with methanol, the natural gas can be subjected to a purification by permeation in order to eliminate, among others, a certain quantity of acid gases while the natural gas proceeding from the washing with methanol and practically exempt of $H_2S$ can be subjected to a treatment of liquefaction. The purified natural gas can also be subjected to a conventional treatment of gasoline removal about which the citation gives no information. Besides, this citation gives no information about the contents of hydrocarbons of the acid gas proceeding from the regeneration of the solvent, it being known that this constitutes an indispensable element for the good operation of the sulphur plants that treat said acid gas.

BRIEF DESCRIPTION OF THE INVENTION

The invention proposes a cryogenic process of simultaneous selective desulphurization and gasoline removal of gaseous mixtures of the type of natural gases, that is, gaseous mixtures under an absolute pressure above 0.5 MPa, which consist mainly of methane and also contain $H_2S$, hydrocarbons having $C_2$ and more, and eventually one or more gaseouss compounds selected among the inert gases, $H_2O$, $CO_2$, COS and mercaptans, said process making it possible to attain more easily and at less expense compared to the already known processes the objective of a separation of the gaseous mixture in the three components, namely, treated gas mainly consisting of methane, liquid fraction of heavy hydrocarbons and stream of acid gases containing $H_2S$, which have the specifications defined above.

The process according to the invention is of the type in which the gaseous mixture is brought into contact in a washing zone with a solvent that with preference dissolves $H_2S$, COS and the mercaptans, but only part of the $CO_2$ and that possesses, on the one hand, a boiling temperature at atmospheric pressure above 40° C. and, on the other hand, a viscosity at $-40°$ C. below 0.1 Pa.s, and there is effected a regeneration of the solvent containing the $H_2S$ and the other compounds absorbed, the process being characterized in that said bringing into contact of the gaseous mixture with the solvent is effected at a sufficiently low temperature and with a ratio of the mass flow rate of gaseous mixture to be treated and of solvent, and a number of theoretical washing steps such as to produce, on the one hand, a treated gas mainly consisting of methane and having a partial pressure in $H_2S$ less than 65 Pa and, when in addition to $H_2S$ the gaseous mixture to be treated likewise contains COS and/or mercaptans, the total partial pressure of the sulphur-containing compounds is less than 260 Pa and, on the other hand, a liquid phase, called rich solvent, composed of the $H_2S$-enriched solvent and other compounds absorbed and of a fraction of condensed hydrocarbons representing at least 80% molar of the hydrocarbons having $C_3$ and more present in the gaseous mixture to be treated, the rich solvent is subjected to a treatment of at least partial removal of methane in order to produce a liquid phase poor in methane and called demethanized rich solvent and a gaseous phase rich in methane, which can be eventually joined to the gaseous mixture to be treated prior to bringing into contact the latter with the solvent, the demethanized rich solvent is cooled at a temperature sufficiently lower than the temperature prevailing in the washing zone for producing a separation of said demethanized solvent in a lower liquid fraction called purified rich solvent that contains the acid compounds $H_2S$ and, should that be the case, COS, $CO_2$ and mercaptans dissolved by the solvent, and possesses a content of hydrocarbons, expressed in methane equivalent, below 5% molar of the quantity of acid compounds dissolved and in an upper liquid fraction called primary fraction of heavy hydrocarbons and formed of the rest of the hydrocarbons that were present in the demethanized rich solvent, the primary fraction of heavy hydrocarbons is separated from the purified rich solvent and said purified rich solvent is subjected to the regeneration treatment for producing a stream of acid gas containing almost all the $H_2S$ and other acid compounds eventually present in the purified rich solvent and containing, expressed in methane equivalent, less than 5% molar of hydrocarbons compared to the desorbed acid compounds and a regenerated solvent that is recycled to the washing zone.

DETAILED DESCRIPTION OF THE INVENTION

Figure 1:
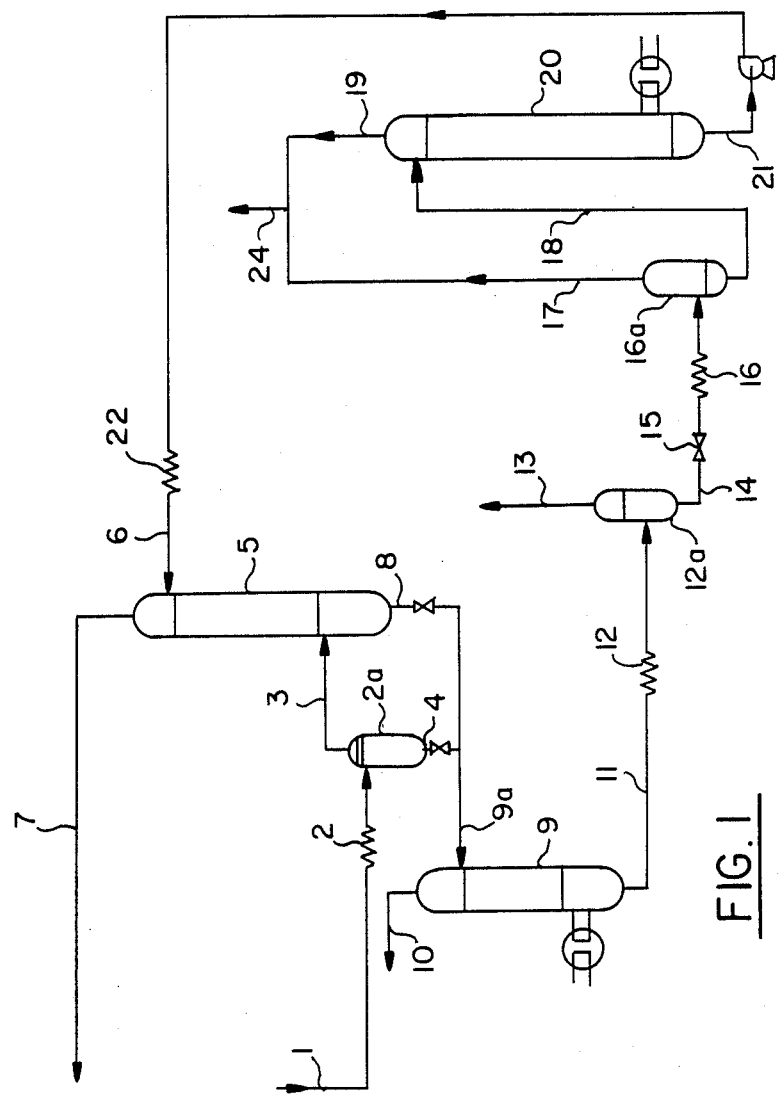

According to the invention, what is designated by "methane equivalent" is as many pseudo-molecules with a single carbon atom as there are carbon atoms in the molecule of hydrocarbon considered.

The solvent, which is generally defined above for the bringing into contact with the gaseous mixture to be treated for purposes of absorption of the H₂S and other COS compounds and mercaptans, preferably possesses a viscosity below 0.05 Pa.s.

The solvent used according to the invention is selective of H₂S, that is to say that it has a capacity of absorption substantially higher for the H₂S and other sulphur-containing compounds cited above than for the CO₂, and for this reason leads to the obtention, in the stream of acid gas produced during the regeneration of the solvent, of a molar ratio H₂S and other sulphur-containing compounds: CO₂ above the ratio that corresponds in the gaseous mixture to be treated.

The solvent according to the invention can in particular consist of one or more liquid absorbents used in the anhydrous form or mixed with water, said solvent or solvents being selected among the amides of the formulae

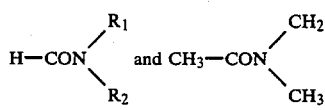

the aldehydes of the formula

the acetals of the formula

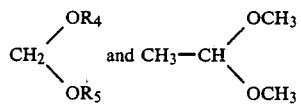

the esters of the formulae

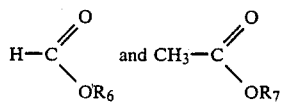

the alkanols having from $C_1$ to $C_4$, the diethers of the formula $CH_3OC_2H_4O_nCH_3$, the diethers alcohols of the formula $R_9O-C_2H_4-O-C_2H_4-OH$, the lactones of the formula

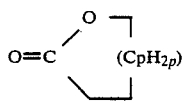

and the propylene carbonate, in these formulae $R_1$ and $R_2$, indentical or different, designating a hydrogen atom or an alkyl radical with $C_1$ or $C_2$, $R_3$ being an alkyl radical having $C_3$ or $C_4$, $R_4$ and $R_5$, identical or different, representing an alkyl radical having from $C_1$ to $C_3$, $R_6$ being an alkyl radical having from $C_2$ to $C_4$ or a radical $C_2H_4O_nR_8$ with $R_8$ designating an alkyl radical having $C_1$ or $C_2$ and an being equal to 1 or 2, $R_7$ being an alkyl radical having $C_1$ or $C_2$ or a radical $C_2H_4O_nR_8$, $R_9$ designating an alkyl radical having from $C_1$ to $C_4$ and p being an integer going from 2 to 4.

Non-limiting examples of liquid organic absorbents corresponding to the above formulae are such as N,N-dimethyl formamide, N,N-dimethyl acetamide, dimethoxy methane, diethoxy methane, dimethoxy-1,1 ethane, methanol, ethanol, dimethyl ether of ethylene glycol, dimethyl ether of diethylene glycol, monomethyl ether of ethylene glycol, butyrolactone, propiolactone and propylene carbonate.

The temperature when the gaseous mixture to be treated is brought into contact with the solvent in the washing zone is preferably comprised between 0° C. and −45° C.

The washing zone consists of one or more washing columns each one advantageously containing at least about 10 and preferably at least 20 theoretical washing stages, said columns being, for example, of the type of columns with plates or also packed columns. In each one of the washing columns the temperature is preferably maintained within ±5° C. by indirect heat exchange effected at one or several points of the column concerned between the fluid medium contained in this column and a cooling fluid.

According to a particular manner of conducting the process according to the invention, the gaseous mixture to be treated is subjected, prior to being brought into contact with the solvent, to a cooling down to a temperature comprised between 0° C. and −30° C. for producing, on one hand, a liquid phase called condensates mainly containing hydrocarbons having $C_3$ and more and H₂S and, on the other hand, a gaseous phase called pre-treated gaseous mixture, said pre-treated gaseous mixture is then put into contact with the solvent in the washing zone and the solvent issued from the washing zone is joined to the condensates issued from the cooling stage for constituting the rich solvent that is subjected to the demethanization treatment.

According to another particular manner of carrying out the process according to the invention, the gaseous mixture to be treated, prior to being brought into contact with the solvent, is subjected to a cooling down to a temperature comprised between 0° C. and −30° C. for producing, on the one hand, a liquid phase called condensates containing mainly hydrocarbons of $C_3$ and more and H₂S and, on the other hand, a gaseous phase called pre-treated gaseous mixture, said pre-treated gaseous mixture is then put into contact with the solvent in the washing zone and each one of the liquid phase constituted by the solvent issued from the washing zone and the condensates issued from the cooling stage is subjected to a separate demethanization treatment and the solvent and the condensates issued from the separate demethanization treatments are joined for constituting the demethanized rich solvent. The gaseous phases produced in the course of the demethanization treatments are preferably recycled, separately or mixed, to the gaseous mixture to be treated upstream of the cooling stage.

The demethanization treatment applied to the rich solvent and to the condensates is advantageously carried out in two stages, namely, a first stage in which the fluid to be demethanized, namely, rich solvent or condensates, is subjected to a first expansion at an intermediate pressure adequate to release a considerable fraction of the methane dissolved in said fluid to be demethanized and to produce a first gas rich in methane and a pre-demethanized fluid and a second stage in which the pre-demethanized fluid is subjected to a second expansion, then to a distillation so as to produce a second gas rich in methane and a demethanized fluid, the second gas rich in methane being compressed up to the pressure of the first gas rich in methane, then mixed with the latter for constituting a gaseous phase rich in methane, which is eventually revealed to the gaseous mixture to be treated. In the second stage of he demethanization treatment, the distillation following the second expansion is preferably effected by re-boiling performed in at least two re-boiling zones arranged in series by means of a fluid consisting either of at least one part of the gaseous mixture to be treated, removed from said gaseous mixture prior to putting in into contact with the solvent or prior to its cooling, or also of part of the regenerated solvent.

The temperature, below the temperature of the demethanized rich solvent, to which said solvent is cooled for producing its separation in to fractions, is advantageously comprised between −25° C. and −80° C.

The purified rich solvent can be regenerated by any treatment such as expansion and/or distillation that allows the release of the gaseous compounds dissolved in a liquid. The regeneration treatment of the purified rich solvent can in particular include a partial regeneration stage comprising an expansion of the purified rich solvent up to a pressure above 100 kPa and preferably between 150 kPa and 300 KPa followed by at least a partial vaporization of said expanded solvent so as to produce, on the one hand, at least a fraction of acid gas and, on the other hand, a semi-regenerated solvent of which the temperature is at least equal to 0° C. and the pressure, below the pressure of the expanded solvent, is at least equal to 100 KPa, then a stage of total regeneration of the semi-regenerated solvent effected by distillation, specially having recourse to a re-boiling, and producing a fraction of acid gas and of the regenerated solvent, said regenerated solvent being recycled, after adequate cooling, to the washing zone while the different fractions of acid gas are joined to form the stream of acid gas the content of hydrocarbons of which, expressed in methane equivalent, is less than 5% molar of the acid compounds.

In the stage of partial regeneration of the purified rich solvent, the partial vaporization of the expanded solvent is advantageously effected by first carrying out a primary partial vaporization of said solvent so as to produce a primary fraction of acid gas and a primary liquid phase having a temperature below 0° C., then effecting a secondary partial vaporization of the primary liquid phase so as to produce a secondary fraction of acid gas and a secondary liquid phase having a temperature at least equal to 0° C. and a pressure below the pressure of the expanded solvent, at least equal to 100 KPa, said secondary liquid phase constituting the semi-regenerated solvent that is treated in the stage of total regeneration, the primary fraction of acid gas being reheated up to a temperature equal to or above 0° C., then joined to the secondary fraction of acid gas and to the fraction of acid gas resulting from the total regeneration of the semi-regenerated solvent to form the stream of acid gas, the hydrocarbons content of which, expressed in methane equivalent, is below 5% molar of the acid compounds.

The total regeneration of the semi-regenerated solvent by distillation is carried out in a column including a plurality of theoretical stages with tapping of the regenerated solvent at the bottom of the column.

In this case the semi-regenerated solvent can be divided into two currents of which one is sent to the head plate of the distillation column and the other feeds said column at the level of an intermediary theoretical stage, after re-heating in counter current with the regenerated solvent drawn off from the column.

Prior to being regenerated, the purified rich solvent can be subjected to a complementary treatment of elimination of the hydrocarbons, said treatment consisting in bringing into contact said purified solvent, in a primary zone of liquid-liquid extraction preferably including at least four theoretical stages of extraction, with an extraction agent mainly constituted by hydrocarbons having a molecular weight higher than that of the n-pentane so as to separate from said purified solvent a secondary liquid fraction of hydrocarbons, joining said secondary fraction with the primary fraction of heavy hydrocarbons, then heating and distilling the mixture thus obtained to produce the fraction of heavy hydrocarbons containing at least 80% molar of the hydrocarbons of $C_3$ and more present in the gaseous mixture to be treated and to recover the extraction agent of which a major portion is recycled to the primary zone of liquid-liquid extraction after cooling to a temperature substantially equal to that reached when the demethanized rich solvent is separated into two fractions.

The treated gas issued from the washing zone is advantageously cooled by at least 15° C. so as to produce a refrigerated treated gas and a liquid fraction which is subjected to the demethanization treatment mixed with the rich solvent. The refrigerated treated gas can also be subjected, in a complementary extraction zone, to an additional extraction by means of the portion of the extraction agent not used in the primary extraction zone so as to produce a treated gas of improved purity and a liquid fraction that is recycled to the distillation of the mixture of primary and secondary fractions of hydrocarbons.

Prior to any treatment, the gaseous mixture to be treated can be subjected to a drying and benzol-removing operation by distillation and contacting with the anhydrous solvent so as to produce, on the one hand, a dry gaseous mixture having a content of aromatic hydrocarbons, specially benzene, less than 0.1% by weight, and, on the other hand, a hydrocarbon fraction containing the major part of the aromatic hydrocarbons contained in the gaseous mixture to be treated and a liquid consisting of solvent containing water.

The invention will be better understood by reading the description given herebelow of three of its embodiments having reference to the installations diagrammatically shown in FIGS. 1 to 4 of the attached drawing.

Referring to FIG. 1, the gaseous mixture to be treated arriving by a conduit 1 undergoes a refrigeration in a cooling zone 2 down to a temperature comprised, for example, between 0° C. and −30° C. and separates, in a separator 2a, on one hand, into a liquid phase called condensates and containing mainly hydrocarbons of $C_3$ and more and $H_2S$, which is drawn off at the bottom of the separator by a conduit 4, and, on the other hand, into a gaseous phase, said pre-treated gaseous mixture exiting at the top of the separator by a conduit 3. Said pre-treated gaseous mixture is introduced at the lower part of a washing column 5 preferably containing at least twenty theoretical washing stages, in which it is put into contact, in counter-current, with a solvent injected in the upper part of the column 5 by a conduit 6, this operation of bringing into contact being effected at a temperature comprised, for example, between 0° C. and −45° C. At the top of the column 5 there is discharged, by a conduit 7, a treated gas mainly consisting of methane and poor in $H_2S$ while at the bottom of said column there is drawn off by a conduit 8 a liquid phase formed of the solvent enriched in $H_2S$ and other absorbed compounds, said liquid phase being joined, in a conduit 9a, to the condensates arriving from the separator 2a by the conduit 4 for constituting a liquid phase called rich solvent. A final temperature within the range 0° C. to −30° C. is selected for the stage of cooling in the zone 2 and the pre-treated gaseous mixture is put into contact with the solvent in column 5 at a temperature sufficiently low within the range 0° C. to −45° C. and with a ratio of the mass flow rates of gaseous mixture to be treated and solvent in a manner such that, on the one hand, the treated gas collected, by the conduit 7 at the top of the column 5 has a partial pressure in $H_2S$ below 65 Pa and, if the gaseous mixture to be treated contains COS and/or mercaptans in addition to $H_2S$, a total partial pressure in sulphur-containing compounds lower than 260 Pa and, on the other hand, the rich solvent passing into the conduit 9a contains at least 80% molar of the hydrocarbons of $C_3$ and more present in the gaseous mixture to be treated.

The rich solvent circulating in the conduit 9a is introduced in the upper part of a demethanization column 9 consisting of a re-boiling distillation column and in which the rich solvent is fractionated in a gaseous phase rich in methane that is discharged at the top of the column 9 by a conduit 10 and in a liquid phase poor in methane, called demthanized rich solvent, which is drawn off at the bottom of the column 9 by a conduit 11. The demethanized rich solvent is led into a cooling zone 12 in which it is cooled to a temperature comprised, for example, between −25° C. and −80° C. and sufficiently lower than the temperature prevailing in the washing zone 5 for producing separation of the demethanized rich solvent into two fractions a, said solvent then separating in a separator 12a, on the one hand, into a lower liquid fraction drawn off from the separator by a conduit 14, said lower fraction, called purified rich solvent, containing the acid compounds $H_2S$, and, should that be the case, $CO_2$, COS and mercaptans dissolved in the solvent and containing less than 5% molar of hydrocarbons, expressed in methane equivalent, in relation to the acid compounds and, on the other hand, into an upper liquid fraction discharged from the separator 12a by a conduit 13, said upper liquid fraction, called primary fraction of heavy hydrocarbons, being formed by the rest of the hydrocarbons that were present in the deemethanized rich solvent and comprising at least 80% molar of the hydrocarbons of $C_3$ and more contained in the gaseous mixture to be treated.

The purified rich solvent then undergoes an expansion up to a pressure above 100 Kpa, preferably comprised between 150 KPa and 300 KPa, by passing through an expansion valve 15, then the expanded solvent crosses a re-heater 16 in which it is made to undergo a partial vaporization, the fluid resulting from said vaporization being led into a separator 16a from which there is discharged at the top, by a conduit 17, a fraction of acid gas and there is drawn off at the bottom, by a conduit 18, a liquid called semi-regenerated solvent. The expansion of the purified rich solvent followed by the partial vaporization of the expanded solvent, which ensure a partial regeneration of the purified rich solvent, are conducted so as to obtain a semi-regenerated solvent having a temperature above or equal to 0° C. and a pressure below the pressure of the expanded solvent and at least equal to 100 KPa. The semi-regenerated solvent passing into the conduit 18 is introduced in the upper part of a column for distillation by re-boiling in which it undergoes a total regeneration. In said column 20, the semi-regenerated solvent is separated, by distillation, into a fraction of acid gas discharged at the top of the column by a conduit 19 and in a regenerated solvent drawn off at the bottom of said column by a conduit 21, said regenerated solvent being recycled by the conduit 6 into the washing column 5 after cooling to an adequate temperature in a cooling zone 22.

The fractions of acid gas discharged respectively at the top of the separator 16a by the conduit 17 and from the column 20 by the conduit 19 are mixed to form the stream of acid gas having a content of hydrocarbons, expressed in methane equivalent, below 5% molar in relation to the acid compounds.

The treated gas, collected by the conduit 7 at the temperature prevailing in the washing zone 5, can be delivered to the distribution network after re-heating or previously undergo, should that be the case, one or more additional treatments such as washing by an adequate solvent for recovering the $CO_2$ that it may still contain, or treatment in a turboexpander for recovering the hydrocarbons of from $C_2$ to $C_3$, which are then joined, after separation from the treated gas, to the fraction of heavy hydrocarbons discharged from the separator 12a by the conduit 13.

Figure 2:
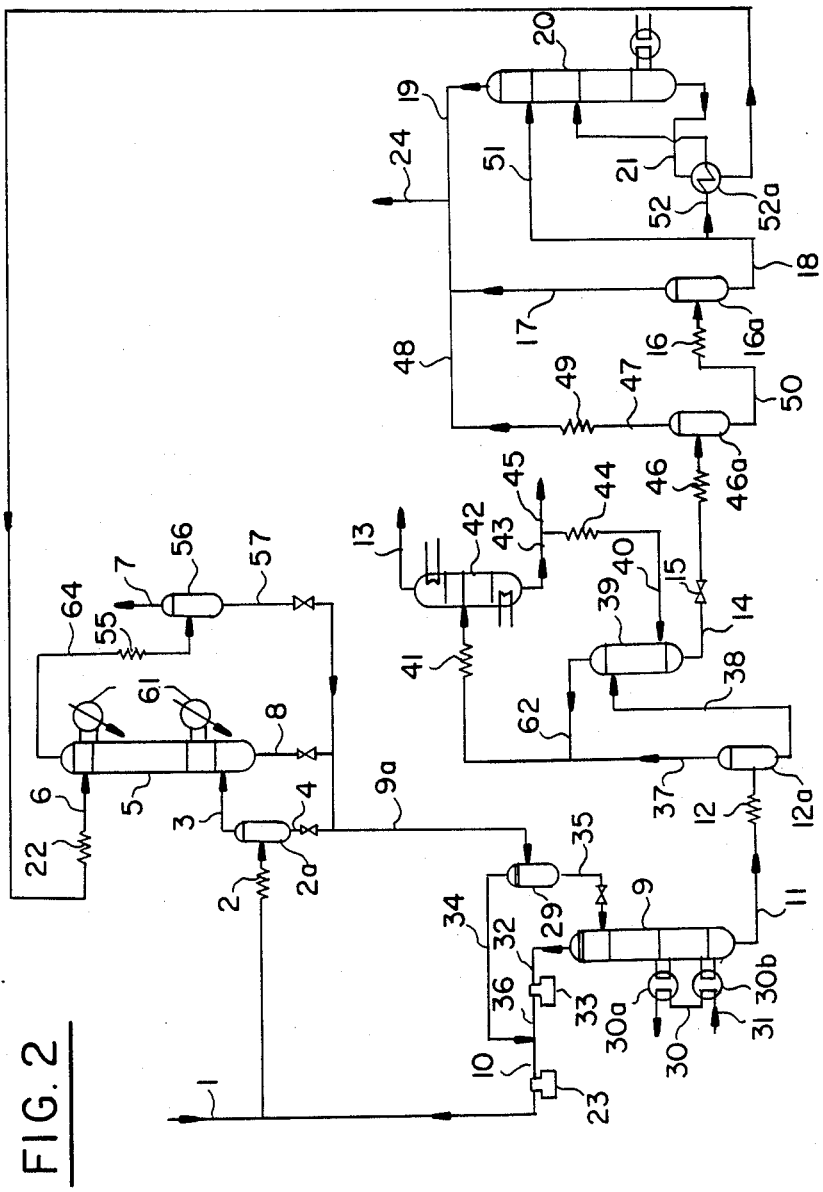

Referring to FIG. 2, the gaseous mixture to be treated that arrives by a conduit 1 undergoes a cooling in a cooling zone 2 down to a temperature comprised, for example, between 0° C. and −30° C. and separates, in a separator 2a, on the one hand, in a liquid phase called condensates and containing mainly hydrocarbons of $C_3$ and more and $H_2S$, said liquid phase being drawn off at the bottom of the separator by a conduit 4 and, on the other hand, in a gaseous phase, said pre-treated gaseous mixture exiting at the top of the separator by a conduit 3. Said pre-treated gaseous mixture is introduced in the lower part of a washing column 5 containing preferably at least twenty theoretical washing stages in which it is put into contact, in counter-current, with a cold solvent injected in the upper part of the column 5 through a conduit 6, said contacting operation being effected at a temperature comprised, for example, between 0° C. and −45° C. At the top of the column 5 there is discharged, by a conduit 64, a treated gas mainly consisting of methane and poor in $H_2S$ while at the bottom of said column there is drawn off, by a conduit 8, a liquid phase formed by the solvent rich in $H_2S$ and other absorbed compounds. The treated gas that circulates in the conduit 64 is cooled by at least 15° C. in a cooling zone 55 and then passes into a separator 56 in which it separates, due to its additional cooling in the zone 55, into a gaseous phase that is collected at the top of the separator 56 by a conduit 7 and into a liquid fraction that is drawn off at the bottom of said separator by a conduit 57. The solvent rich in $H_2S$ and other acid compounds that is drawn off by the conduit 8 from the column 5 and the condensates issued from the separator 2a by the conduit 4 are mixed for constituting a liquid phase called rich solvent to which is added the liquid fraction issued from the separator 56 by the conduit 57, the combination flowing into the conduit 9a. A final temperature within the range 0° C. to −30° C. is selected for the cooling stage in the zone 2 and the pre-treated gaseous mixture is put into contact with the solvent in column 5 at a temperature sufficiently low within the range 0° C. to −45° C. and with a ratio of the flow rates of gaseous mixture to be treated and of solvent in a manner such that, on the one hand, the treated gas collected by the conduit 64 at the top of the column 5 has a partial pressure in $H_2S$ below 65 Pa and, if the gaseous mixture to be treated contains COS and/or mercaptans in addition to $H_2S$, a total partial pressure in sulphur-containing compounds below 260 Pa and, on the other hand, the rich solvent passing into the conduit 9a contains at least 80% molar of hydrocarbons of $C_3$ and more present in the gaseous mixture to be treated. The column 5 includes two coolers 61 traversed by the fluid medium, namely, mixture of solvent and of gas to be treated, contained in said column and allowing said medium indirectly to exchange calories with a cooling fluid so as to limit the heating of said medium due to the absorption and to obtain a uniform profile of temperature within ±5° C. in the column.

The rich solvent circulating in the conduit 9a is introduced in the upper part of an expansion zone 29 so as to effect an expansion of said rich solvent to an intermediate pressure adequate to release a considerable fraction of the methane dissolved in the rich solvent and to produce a first gas rich in methane that is discharged at the top of the zone 29 by a conduit 34 and a pre-demethanized rich solvent that is drawn off at the bottom of the zone 29 by a conduit 35. Said predemethanized rich solvent is subjected to a second expansion followed by a distillation in a distillation column 9 including a reboiler zone so comprising two re-boilers 30a and 30b situated in series by means of a re-boiling fluid 31 consisting either of at least one portion of the gaseous mixture to be treated or also of a portion of the regenerated solvent so as to produce a second gas rich in methane that is dischered at the top of the column 9 by a conduit 32 and a liquid phase poor in methane, called demethanized rich solvent, which is drawn off at the bottom of the column 9 by a conduit 11. The second gas rich in methane that circulates in the conduit 32 is led to pass in a compressor 33 from which it exits, by a conduit 36, at a pressure substantially equal to that of the first gas rich in methane that passes into the conduit 34, then these two gases rich in methane are mixed in the conduit 10 and the gaseous phase resulting from this mixture is recycled by means of a compressor 23 into the gaseous mixture to be treated arriving by the conduit 1.

The demethanized rich solvent is introduced in a cooling zone 12 in which it is cooled to a temperature comprised, for example, between −25° C. and −80° C. and sufficiently below the temperature prevailing in the washing zone 5 for producing the separation of said demethanized rich solvent in two fractions which separate in a separator 12a into a lower liquid fraction drawn off from the separator by a conduit 38, said fraction being called pre-purified solvent and consisting of a solution of $H_2S$ acid compounds, and should that be the case, $CO_2$, COS and mercaptans in the solvent, said solution containing likewise a small quantity of hydrocarbons, and into an upper liquid fraction, called primary fraction of heavy hydrocarbons, which is discharged from the separator 12a by a conduit 37. The pre-purified solvent is then introduced in the upper part of a primary zone 39 of liquid-liquid extraction which includes at least four theoretical extraction stages and in which said solvent is put into contact, in counter-current, with an extraction agent introduced in the lower part of the zone 39 by a conduit 40.

The extraction agent consists mainly of hydrocarbons having a moledular weight higher than that of n-pentane. The extraction operation results in separating a liquid secondary fraction of hydrocarbons, which is discharged from the extraction zone 39 by a conduit 62, from a purified rich solvent which is drawn off from the extraction zone 39 by a conduit 14 and contains in solution the acid compounds $H_2S$, and, should that be the case, $CO_2$, COS and mercaptans and less than 5% molar of hydrocarbons expressed in methane equivalent, in relation to the acid compounds. The secondary fraction of hydrocarbons that passes into the conduit 62 is joined to the primary fraction of hydrocarbons that flow by the conduit 37 and the mixture thus obtained is led, through a heater 41, into a distillation column 42 wherein said mixture is fractionated so as to discharge, at the top of the column 42 by a conduit 13, a fraction of heavy hydrocarbons containing at least 80% molar of the hydrocarbons of $C_3$ and more present in the gaseous mixture to be treated and to recover at the bottom of said column, by a conduit 43, the extraction agent of which a major portion is recycled to the extraction zone 39 by the conduit 40 after cooling in a cooling zone 44 at a temperature substantially equal to that prevailing in the separation zone 12. The remaining portion of the extraction agent is discharged by a conduit 45.

The purified rich solvent flowing in the conduit 14 then undergoes an expansion to a pressure above 100 KPa and preferably comprised between 150 KPa and 300 KPa by passing through an expansion valve 15, then the expanded solvent passes through a primary heater 46 wherein it is caused to undergo a primary partial vaporization and the fluid resulting from said primary vaporization is led to a separator 46a from the top of which is discharged, by a conduit 47, a primary fraction of acid gas and from the bottom is drawn off, by a conduit 50, a primary liquid phase having a temperature below 0° C. Said primary liquid phase then passes into a secondary heater 16 wherein it is subjected to a secondary partial vaporization, and the fluid resulting from said secondary vaporization is introduced in a separator 16a at the top of which is discharged, by a conduit 17, a second fraction of acid gas and at the bottom is drawn off, by a conduit 18, a secondary liquid phase called semi-regenerated sovent having a temperature equal to or higher than 0° C. and the pressure is below the pressure of the expanded solvent and at least equal to 100 KPa. This succession of operations constitutes the stage of partial regeneration of the purified rich solvent. The semi-regenerated solvent is then subjected to a stage of total regeneration. To do this, the semi-regenerated solvent that exits from the separator 16a by the conduit 18 is divided in two stream of which one is introduced by a conduit 51 on the top plate of a distillation column 20 by re-boiling including a plurality of theoretical stages and the other is injected in said column at an intermediate point of the latter, by a conduit 52, after having been heated in an indirect heat exchanger 52a. In the column 20 the semi-regenerated solvent is separated by distillation into a fraction of acid gas discharged at the top of the column by a conduit 19 and a regenerated solvent drawn off at the bottom of said column by a conduit 21, said regenerated solvent being used, in the heat exchanger 52a, to heat the current of semi-regenerated solvent injected in the column 20 by the conduit 52 prior to being recycled, by a conduit 6, into the washing column 5 through a cooling zone 22, which ensures a cooling of the regenerated solvent to a temperature adequate for its injection in the column 5.

The primary fraction of acid gas discharged from the separator 46a by the conduit 47 is brought to a temperature higher than or equal to 0° C. in a heater 49, then it flows in a conduit 48 for being mixed with the secondary fraction of acid gas discharged from the separator 16a by the conduit 17 and with the fraction of acid gas discharged from the column of total regeneration 20 by the conduit 19, the mixture of said three fractions of acid gas constituting the stream of acid gas produced by the process and having a content of hydrocarbons, expressed in methane equivalent, below 5% molar compared to the acid compounds.

The treated gas collected by the conduit 7 at the temperature prevailing in the separator 56 can be delivered to the distribution network after heating or undergo previously, if desired, one or more additional treatments, as indicated above for the embodiment referring to FIG. 1.

Figure 3:
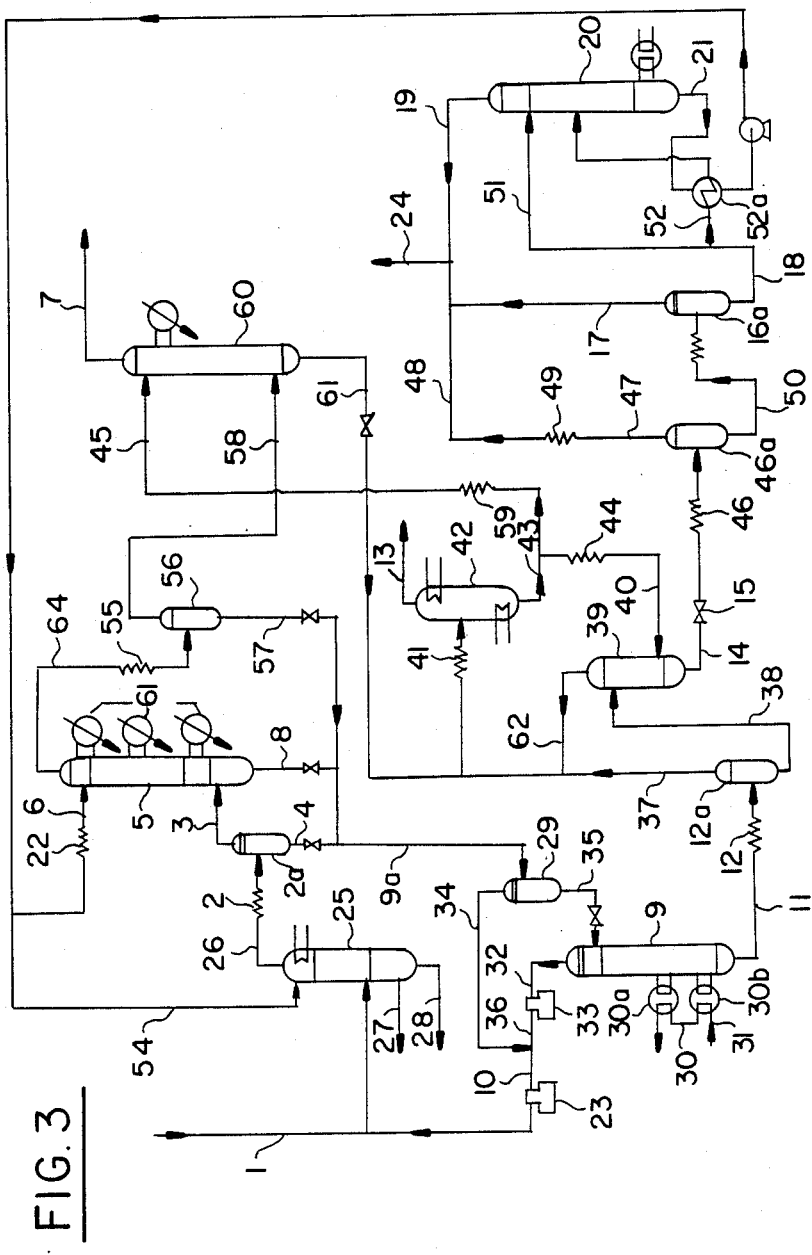

The embodiment of the process according to the invention that is illustrated by FIG. 3 includes all the stages of the embodiment referring to FIG. 2 to which are added a stage of drying and benzol removal carried out on the gaseous mixture to be treated prior to any other operation and an additional purification stage by extraction effected on the cooled treated gas collected at the top of the separator 56.

The gaseous mixture to be treated that arrives by the conduit 1 is introduced in the lower part of a re-boiling column 25 in which said gaseous mixture is put into contact, in counter-current, with solvent removed by a conduit 54 discharging in the upper part of the column 25 on the regenerated solvent upstream of the heat exchanger 52a and prior to passage of said solvent into the cooling zone 22 so as to produce, on one hand, a dry gaseous mixture discharged from the column 25 by a conduit 26 and having a content of aromatic hydrocarbons, specially benzene, below 0.1% by weight, and, on the other hand, an aromatic hydrocarbon fraction drawn off from the column 25 by a conduit 27 and containing the major portion of the aromatic hydrocarbons contained in the gaseous mixture to be treated and a liquid drawn off from the column 25 by a conduit 28 and consisting of solvent containing the water absorbed.

The dry gaseous mixture circulating in the conduit 26 is then subjected to the same treatment as the gaseous mixture arriving by the conduit 1 in the embodiment of FIG. 2, but with, on one hand, utilization in the washing column 5 of three cooling zones 61 for control of the temperature in said column, and, on the other hand, recycling of the gaseous phase rich in methane which issues from the demethanization and flows in the conduit 10 in the gaseous mixture to be treated prior to being introduced in the drying and benzol-removing column 25.

The cooled treated gas issued from the separator 56 is led, by a conduit 58, into the lower part of a complementary extraction zone 60 wherein it is put into contact, in counter-current, with an extraction agent introduced in the upper part of said column so as to produce a treated gas of improved purity discharged at the top of the column 60 by a conduit 7 and a liquid fraction that is drawn off, by a conduit 61, at the bottom of said zone and that is joined to the mixture of primary and secondary fractions of hydrocarbons introduced in the heater 41. As the extraction agent injected in the extraction zone 60, there is used the portion of the extraction agent drawn off from the distillation column 42 that has not been used for feeding the primary extraction zone 39 after having cooled it in a cooling zone 59.

The treated gas collected by the conduit 7 at the temperature prevailing in the extraction zone 60 can be delivered to the distribution network after heating or previously undergo, if desired, one or more additional treatments, as indicated for the embodiments referring to FIGS. 1 and 2.

Figure 4:
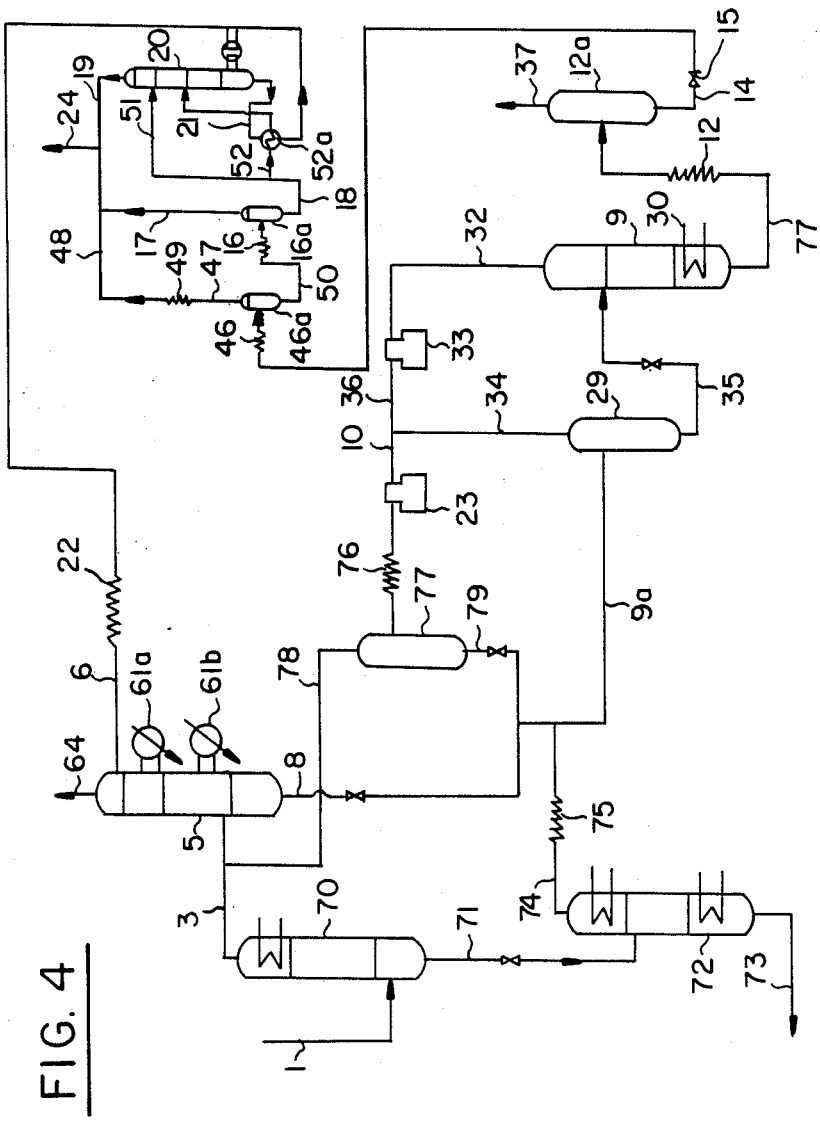

Referring to FIG. 4, the gaseous mixture to be treated that arrives by a conduit 1 is introduced in the lower part of a tower 70 wherein it is cooled to a temperature comprised, for example, between 0° C. and −30° C., and separates, on one hand, in a liquid phase called condensates and containing mainly hydrocarbons of $C_3$ and more and $H_2S$, said liquid phase being drawn off at the bottom of the tower 70 by a conduit 71 and, on the other hand, in a gaseous phase, said pre-treated gaseous mixture exiting at the top of the tower 70 by a conduit 3. Said pre-treated gaseous mixture is introduced in the lower part of a washing column 5 containing, preferably, at least twenty theoretical washing stages, in which it is put into contact, in counter-current, with a cold solvent injected in the upper part of said column 5 by a conduit 6, said contacting being effected at a temperature comprised, for example, between 0° C. and −45° C. At the top of the column 5 there is discharged, by a conduit 64, a treated gas consisting mainly of methane and poor in $H_2S$ while at the bottom of said column there is drawn off, by a conduit 8, a liquid phase formed by the solvent rich in $H_2S$ and other absorbed compounds.

The liquid phase drawn off from the tower 70 by the conduit 71 is distilled in a column 72 so as to produce condensates drawn off at the bottom of said column by a conduit 73, and a gaseous phase which is discharged from the column 72 by a conduit 74, then cooled in a cooling zone 75 prior to being mixed with the enriched solvent that circulates in the conduit 8 for forming a liquid phase called rich solvent, which flows in the conduit 9a. For the stage of cooling in the tower 70, a temperature within the range from 0° C. to −30° C. is selected and the contacting of the pre-treated gaseous mixture with the solvent in the column 5 is effected at a temperature sufficiently low within the range from 0° C. to −45° C. and with a ratio of the mass flow rates of gaseous mixture to be treated and of solvent in a manner such that, on one hand, the treated gas collected by the conduit 64 at the top of the column 5 has a partial pressure in $H_2S$ below 65 Pa and, if the gaseous mixture to be treated contains COS and/or mercaptans in addition to $H_2S$, a total partial pressure in sulphur-containing compounds below 260 Pa, and, on the other hand, the rich solvent passing into the conduit 9a contains at least 80% molar of hydrocarbons of $C_3$ and more present in the gaseous mixture to be treated. The column 5 includes two cooling zones 61a and 61b traversed by the fluid medium, namely, mixture of solvent and of gas to be treated, contained in said column and allowing said medium to exchange indirectly calories with a cooling fluid so as to limit the heating of said medium due to the absorption and to obtain a uniform profile of temperature in the column.

The rich solvent circulating in the conduit 9a is introduced in the upper part of an expansion zone 29 so as to perform an expansion of said rich solvent at an intermediate pressure adequate to release a considerable fraction of the methane dissolved in the rich solvent and to produce a first gas rich in methane that is discharged at the top of the expansion zone 29 by a conduit 34 and a pre-demethanized rich solvent that is drawn off at the bottom of the expansion zone 29 by a conduit 35. Said pre-demethanized rich solvent is subjected to a second expansion followed by a distillation in a distillation column 9 including a boiling system 30 so as to produce a second gas rich in methane that is discharged at the top of the column 9 by a conduit 32 and a liquid phase poor in methane, called demethanized rich solvent, which is drawn off at the bottom of the column 9 by a conduit 11. The second gas rich in methane that circulates in the conduit 32 is led to pass into a compressor 33 from which it exits, by a conduit 36, at a pressure substantially equal to that of the first gas rich in methane that passes into the conduit 34, then said two gases rich in methane are mixed in the conduit 10 and the gaseous phase resulting from this mixture is introduced, by means of a compressor 23, in a cooling zone 76 wherein said gaseous phase is brought to a temperature substantially equal to that of the pre-treated gaseous mixture that circulates in the conduit 3. The gaseous phase issued from the cooling zone 76 is partially liquefied. Said partially liquefied phase is introduced in a separator 77 wherein it separates into a liquid fraction that is drawn off from the separator by a conduit 79 and mixed with the enriched solvent passing in the conduit 8 and in a gaseous fraction, which is discharged from the separator 77 by a conduit 78 and incorporated into the pre-treated gaseous mixture passing in the conduit 3.

The demethanized rich solvent is introduced in a cooling zone 12 wherein it is cooled to a temperature comprised, for example, between $-25°$ C. and $-80°$ C. and sufficiently below the temperature prevailing in the washing zone 5 to produce a separation of said demethanized rich solvent into two fractions, which separate in a separator 12a in a lower liquid fraction drawn off from the separator by a conduit 14, said fraction being called purified solvent and consisting of a solution of acid compounds $H_2S$, and, should that be the case, $CO_2$, COS and mercaptans in the solvent, said solution containing likewise a very small quantity of hydrocarbons, and in an upper liquid fraction called primary fraction of heavy hydrocarbons which is discharged from the separator 12a by a conduit 37.

The purified rich solvent flowing in the conduit 14 is then subjected to regeneration treatment, as indicated with reference to FIG. 2, for producing, on one hand, the regenerated solvent, which is recycled by a conduit 6 into the washing column 5 through a cooling zone 22 ensuring a cooling of the regenerated solvent to a temperature adequate for being injected in the column 5 and, on the other hand, the stream of acid gas 24 furnished by the process and containing a quatity of hydrocarbons, expressed in methane equivalent, below 5% molar in relation to the acid compounds.

For completing the preceding description, there are given herebelow four nonlimiting examples of conducting the process according to the invention.

EXAMPLE 1

Making use of an installation analogous to the one diagrammatically shown in FIG. 2 of the attached drawing and operating as described above, there was treated a gaseous mixture having the following molar composition:

| | |
|---|---|
| methane | 69% |

-continued

| | |
|---|---|
| ethane | 3% |
| propane | 1% |
| butane | 1% |
| hexane | 1% |
| $H_2S$ | 15% |
| $CO_2$ | 10% |

The gaseous mixture to be treated, arriving by the conduit 1 with a delivery of 20,000 Kmoles/hour, a temperaturre of 30° C. and a pressure of 5 MPa, was mixed with the gaseous phase rich in methane issued from the demethaniztion of the rich solvent and delivered by the compressor 23, and the gaseous mixture obtained was cooled down to $-10°$ C. in the cooling zone 2. This cooling produced 872 Kmoles/h of condensates discharged from the separator 2a by the conduit 4 and 21,039 Kmoles/h of pre-treated gas discharged from the separator 2a by the conduit 3 and having the following molar composition:

| | |
|---|---|
| methane | 70.31% |
| ethane | 3.20% |
| propane | 0.85% |
| butane | 0.51% |
| hexane | 0.11% |
| $H_2S$ | 13.89% |
| $CO_2$ | 11.13% |

The pre-treated gaseous mixture was put into contact with 14,000 Kmoles/h of solvent consisting of pure methanol, said contacting having been effected in a washing column 5 including 28 theoretical stages and provided with two lateral coolers 61 of which one is situated at the level of the first plate and the other at the level of the 28th plate and having respective energies of 40 and 37.8 G Joules/hour, which makes it possible to limit the heating due to the absorption and to obtain a uniform temperature profile within $\pm 5°$ C. in the column 5, said column operating at a temperature of $-10°$ C.

At the top of the column 5 was discharged a treated gas having a pressure of 4959 KPa and a temperature of $-10°$ C. and the following composition in molar percentage:

| | |
|---|---|
| methane | 91.71 |
| ethane | 2.99 |
| propane | 0.15 |
| butane | 0 |
| hexane | 0 |
| $H_2S$ | 10 p.p.m. (by volume) |
| $CO_2$ | 5.06 |
| methanol | 0.09 |

The partial pressure in $H_2S$ of said treated gaseous mixture was equal to 50 Pa.

The treated gaseous mixture issued from the column 5 by the conduit 64 was cooled down to $-45°$ C. in the cooling zone 55 so as to condense, in the separator 56, more than 90% of the methanol taken along by the gaseous mixture out of the washing column 5. The liquid fraction, condensed in the separator 56 and drawn off from said separator by the conduit 57 with a delivery of 15 Kmoles/h, contained mainly methanol and $CO_2$.

The condensates drawn off from the separator 2a by the conduit 4, the solvent rich in acid compounds drawn off from the column 5 by the conduit 8, and the liquid fraction drawn off from the separator 56 by the conduit 57 were mixed to constitute the rich solvent subjected to demethanization, said rich solvent having a delivery equal to 21,270 Kmoles/h and the following composition in molar percentage:

| | |
|---|---|
| methane | 5.96 |
| ethane | 1.34 |
| propane | 0.96 |
| butane | 0.99 |
| hexane | 0.95 |
| methanol | 65.82 |
| $H_2S$ | 15.91 |
| $CO_2$ | 8.05 |

The demethanization of the rich solvent included in the first place a first expansion of said solvent to a pressure of 2420 Kpa in the expansion zone 29 making it possible to separate 61% of the methane dissolved with production of 1149 Kmoles/h of a gas containing 68% molar of methane discharged at the top of the expansion zone 29 by the conduit 34 and a pre-demethanized rich solvent drawn off from said expansion zone by the conduit 35, then a second expansion to 1050 KPa of the pre-demethanized rich solvent followed by a distillation in the column 9 including 11 theoretical plates, the re-boiling thereof being effected by the gaseous mixture to be treated so as to produce 1148 Kmoles/h of a second gas rich in methane discharged at the top of the column 9 by the conduit 32 and the demethanized rich solvent available at 13° C. and 1070 KPa having the following composition in molar percentage:

| | |
|---|---|
| methane | 0.02 |
| ethane | 0.79 |
| propane | 0.94 |
| butane | 1.05 |
| hexane | 1.05 |
| methanol | 73.76 |
| $H_2S$ | 15.81 |
| $CO_2$ | 6.54 |

The second gas rich in methane was compressed in the compressor 33 to 2420 KPa, then mixed with the first gas rich in methane to constitute the gaseous phase rich in methane recycled in the gaseous mixture to be treated by means of the compressor 23.

The demethanized rich solvent was cooled in the cooling zone 12 down to a temperature of −75° C. to separate it into two fractions that separated in the separator 12a into a primary fraction of heavy hydrocarbons discharged by the conduit 37 and a pre-purified solvent drawn off by the conduit 38.

Said pre-purified solvent had the following composition in molar percentage:

| | |
|---|---|
| methane | 0.02 |
| ethane | 0.55 |
| propane | 0.58 |
| butane | 0.45 |
| hexane | 0.09 |
| methanol | 76.20 |
| $H_2S$ | 15.54 |
| $CO_2$ | 6.58 |

The pre-purified solvent circulating in the conduit 38 was put into contact, in the liquid-liquid extraction device 39 including 5 theoretical stages and operating at −75° C., with 600 Kmoles/h of an extraction agent mainly composed of hexane, the result of said extraction being the production of a secondary liquid fraction of hydrocarbons discharged from the device 39 by the conduit 62 and of a purified solvent drawn off by the conduit 14.

Said purified solvent had the following composition in molar percentage:

| | |
|---|---|
| methane | 0.01 |
| ethane | 0.08 |
| propane | 0.04 |
| butane | 0.01 |
| hexane | 0.12 |
| methanol | 79.08 |
| $H_2S$ | 15.54 |
| $CO_2$ | 6.40 |

The secondary fraction of hydrocarbons passing in the conduit 62 was joined to the primary fraction of hydrocarbons flowing through the conduit 37 and the mixture thus obtained was heated in the heater 41, then fractionated by distillation in the column 42 into a fraction of heavy hydrocarbons discharged by the conduit 13 and containing 96% molar of the hydrocarbons of $C_3$ and more contained in the gaseous mixture to be treated arriving by the conduit 1 and a liquid fraction consisting of the extraction agent and drawn off by the conduit 43. A major portion of said extraction agent was cooled down to −75° C. by passage into the cooling zone 44, then recycled toward the extraction device 39 by the conduit 40.

The purified rich solvent flowing through the conduit 14 was subjected to a regeneration treatment including a stage of partial regeneration followed by a stage of total regeneration. For carrying out the stage of partial regeneration, said purified rich solvent was expanded to 230 KPa by traversing the expansion valve 15, then it underwent a primary partial vaporization in the heater 46 by heating to −25° C. with the result of the separation in the separator 46a of 1767 Kmoles/h of a primary fraction of acid gas collected by the conduit 47 from a primary liquid phase drawn off by the conduit 50. Said liquid phase then underwent a secondary partial vaporization in the heater 16 by heating to 70° C. under a pressure of 190 KPa having as result the separation, in the separator 16a, of 1133 Kmoles/h of a secondary fraction of acid gas discharged by the conduit 17 from a semi-regenerated solvent drawn off by the conduit 18 and having a temperature equal to 7° C.

The total regeneration of the semi-regenerated solvent was carried out by first pumping said solvent up to 450 KPa and then dividing it into two streams. One of the streams, representing a delivery of 5000 Kmoles/h, was sent by the conduit 51 to the top plate of the distillation column 20 which operates under a pressure of 350 KPa while the other current was heated in the heater 52a to 88° C. by indirect heat exchange with the regenerated solvent drawn off from the column 20 by the conduit 21, and was then introduced in the column 20 at the level of the seventh theoretical stage. The distillation of the semi-regenerated solvent in the column 20 produced 799 Kmoles/h of a fraction of acid gas collected by the conduit 19 and of regenerated solvent drawn off by the conduit 21. Said regenerated solvent left the heat exchanger 52a with a temperature of 30° C. and was recycled in the column 5 by the conduit 6, after cooling down to −10° C. in the cooling zone 22.

The primary fraction of acid gas flowing in the conduit 47 was brought to a temperature of 7° C. in the heater 49, it was then joined to the secondary fraction of acid gas passing in the conduit 17 and to the fraction of acid gas discharged from the column 20 by the conduit 19 to form a stream of acid gas having a pressure of 190 KPa and a delivery of 3699 Kmoles/h, said stream of acid gas having in addition a content of hydrocarbons, expressed in methane equivalent, equal to 1.9% molar and a methanol content of 1.14% by weight. The molar ratio $H_2S:CO_2$ in the stream of acid gas was equal to 2.22 whereas the value of this same ratio in the gaseous mixture to be treated was only 1.5.

The current of acid gas flowing through the conduit 24 was then subjected to a conventional washing with water prior to being led toward a sulphur unit CLAUS.

EXAMPLES 2 TO 4

Using an installation analogous to the one diagrammatically shown in FIG. 4 of the attached drawing and operating as described above, there was treated a gaseous mixture having a composition, a delivery, a temperature and a pressure identical with those of the gaseous mixture treated in Example 1.

The solvent used changed from one example to the other and consisted of pure propylene carbonate (Example 2), pure dimethyl formamide (Example 3) and pure α butyrolactone (Example 4).

The mode of operation that follows was used in the three examples.

The gaseous mixture to be treated was cooled down to −24° C. in the tower 70, this cooling producing 1226 Kmoles/h of condensates drawn off by the conduit 71 and 18774 Kmoles/h of pre-treated gaseous mixture exiting from the tower 70 by the conduit 3.

Said pre-treated gas had the following composition in molar percentage in the three examples.

| | |
|---|---|
| methane | 72.35 |
| ethane | 2.96 |
| propane | 0.79 |
| butane | 0.02 |
| hexane | 0. |
| $H_2S$ | 13.67 |
| $CO_2$ | 10.21 |

The washing column 5, where the pre-treated gaseous mixture was put into contact with the solvent, included 21 theoretical stages and was equipped with two cooling zones 61a and 61b respectively situated on the 11th and 21st plates, the energies of said coolants being chosen for limiting the heating due to the absorption and obtaining a uniform temperature profile in said column within ±50° C.

There was discharged at the top of the column 5 by the conduit 64 a treated gas having a pressure of 4950 kPa and an $H_2S$ content corresponding to a partial pressure of $H_2S$ equal to 5 Pa.

At the bottom of the column 5 there was drawn off, by the conduit 8, a liquid phase formed of the solvent rich in $H_2S$ and other absorbed compounds.

The condensates formed in the tower 70 were distilled in the column 72 with the production of new condensates drawn off from said column by the conduit 73 and of a gas that was cooled down to −25° C. in the cooling zone 75, then mixed with the enriched solvent passing in the conduit 8 to undergo the demethanization.

The rich solvent circulating in the conduit 9a was demethanized in two stages. First an expansion to a pressure of 2450 kPa in the expansion zone 29 made it possible to separate about 80% of the methane dissolved in said solvent. This expansion produced a first gas rich in methane discharged by the conduit 34 and a pre-demethanized rich solvent drawn off by the conduit 35. A second expansion to 1000 kPa followed by a distillation in the distillation column 9 equipped with 14 theoretical plates produced a second gas rich in methane discharged by the conduit 32 and a demethanized rich solvent available in th conduit 11 at a temperature of 5° C. and under a pressure of 1000 kPa. The second gas rich in methane was compressed to 2400 kPa in the compressor 33, then admixed to the first gas rich in methane in the conduit 10, the resulting mixture being then compressed to 5500 kPa in the compressor 23. The compressed gas rich in methane issued from the compressor 23 passed in the cooling zone 76 where it was cooled down to −25° C. and partially liquefied, the partially liquefied fluid issued from the zone 76 being introduced in the separator 77. The gaseous fraction discharged from said separator by the conduit 78 was incorporated into the pre-treated gaseous mixture introduced in the washing column 5, while the liquid phase drawn off from the separator by th conduit 79 was admixed to the enriched solvent flowing from the column 5 through the conduit 8.

The demethanized rich solvent flowing through the conduit 11 was cooled in the cooling zone 12 to separate into two fractions that separate in the separator 12a into one liquid fraction of hydrocarbons discharged by the conduit 37 and a purified solvent drawn off by the conduit 14.

The purified solvent was then subjected to a regeneration treatment including a partial regeneration stage followed by a total regeneration stage, as described in Example 1 in order, on one hand, to furnish through the conduit 24 a stream of acid gas with a very small content of hydrocarbons and, on the other hand, to produce, by the conduit 21, a regenerated solvent, which after cooling down to −25° C. in the cooling zone 22 was recycled to the washing column 5 by the conduit 6.

The operating conditions and the specific results of each example are given in the table that follows.

TABLE

| EXAMPLE | 2 | 3 | 4 |
|---|---|---|---|
| solvent | propylene carbonate | dimethyl-formamide | γbutyrolactone |
| delivery of the solvent arriving by 6 to the column 5 (Kmoles/h) | 5,500 | 2,500 | 5,000 |
| energy of the cooler in G Joules/h | | | |
| 61a: | 2 | 8 | 10 |
| 61b: | 29 | 35 | 30 |
| treated gas discharged | | | |

TABLE-continued

| EXAMPLE | 2 | 3 | 4 |
|---|---|---|---|
| by the conduit 64 | | | |
| temperature: | −25° C. | −15° C. | −25° C. |
| molar composition (%) | | | |
| methane | 89.65 | 88.06 | 89.65 |
| ethane | 3.45 | 3.33 | 3.45 |
| propane | 0.80 | 0.74 | 0.80 |
| butane | 0. | 0. | 0. |
| hexane | 0. | 0. | 0. |
| $H_2S$ | 1 ppm (V/V)* | 1 ppm (V/V) | 1 ppm (V/V) |
| $CO_2$ | 6.10 | 7.86 | 6.10 |
| solvent | 0.3 ppm (V/V) | 1 ppm (V/V) | 0.3 ppm (V/V) |
| enriched solvent drawn off by 8 | | | |
| Delivery (Kmoles/h) | 9,410 | 6,160 | 8,910 |
| molar composition (%) | | | |
| methane | 2.77 | 4.42 | 2.92 |
| ethane | 0.46 | 0.86 | 0.48 |
| propane | 0.29 | 0.60 | 0.31 |
| butane | 0.02 | 0.04 | 0.02 |
| solvent | 58.44 | 40.58 | 56.14 |
| $H_2S$ | 27.76 | 41.67 | 28.79 |
| $CO_2$ | 10.74 | 11.84 | 11.34 |
| demethanization | | | |
| first gas rich in methane discharged by 34 | | | |
| molar content of methane (%) | 62 | 62 | 62 |
| delivery (Kmoles/h) | 816 | 990 | 800 |
| second gas rich in methane discharged by 32 | | | |
| delivery (Kmoles/h) | 553 | 881 | 500 |
| demethanized rich solvent drawn off by 11 | | | |
| molar composition (%) | | | |
| propane | 0.45 | 0.85 | 0.50 |
| butane | 0.03 | 0.05 | 0.03 |
| hexane | 0. | 0. | 0. |
| solvent | 58.43 | 41.18 | 56.09 |
| $H_2S$ | 31.04 | 48.28 | 32.78 |
| $CO_2$ | 10.04 | 9.63 | 10.60 |
| cooling of the demethanized solvent in zone 12 | | | |
| temperature reached | −45° C. | −50° C. | −45° C. |
| purified solvent drawn off by 14 | | | |
| molar composition (%) | | | |
| propane | 0.10 | 0.17 | 0.10 |
| butane | 0.02 | 0.05 | 0.02 |
| hexane | 60. | 0. | 0. |
| solvent | 60.88 | 42.28 | 58.71 |
| $H_2S$ | 30.62 | 49.04 | 32.33 |
| $CO_2$ | 8.37 | 8.45 | 8.84 |
| regeneration of the purified solvent regenerated solvent drawn off by 21 | | | |
| delivery (Kmoles/h) | 5,500 | 2,500 | 5,000 |
| $H_2S$ content | 1 ppm (V/V) | 1 ppm (V/V) | 1 ppm (V/V) |
| acid gas discharged by 24 | | | |
| delivery (Kmoles/h) | 3,533 | 3,533 | 3,533 |
| molar composition (%) | | | |
| propane | 0.25 | 0.29 | 0.25 |
| butane | 0.06 | 0.08 | 0.08 |
| $H_2S$ | 78.29 | 84.97 | 78.28 |
| $CO_2$ | 21.40 | 14.65 | 21.41 |

*ppm (V/V) = portion per million in volume

We claim:

1. A process for removing sulphur containing compounds and recovering hydrocarbons having at least three carbon atoms from a gaseous mixture comprising methane, hydrocarbons having at least two carbon atoms and acid gas compounds comprising $H_2S$ which comprises:

(a) contacting the gaseous mixture, at an absolute pressure above about 0.5 MPa and a sufficiently low temperature, with an amount of a solvent, to provide a treated gas containing methane and a partial pressure of $H_2S$ not higher than 65 Pa, and a rich solvent comprising $H_2S$ and at least 80 molar percent of the hydrocarbons having at least three carbon atoms in the gaseous mixture, the solvent being a solvent for $H_2S$, having a boiling point at atmospheric pressure above 40° C. and a viscosity at −40° C. less than 0.1 Pa.s;

(b) demethanizing the rich solvent to provide a demethanized rich solvent and a gas rich in methane;

(c) cooling the demethanized rich solvent to a temperature at which the demethanized rich solvent separates into a purified rich solvent containing acid gas compounds and an amount of hydrocarbon, expressed as methane equivalent, less than about 5 molar % of the acid gas compounds and a primary fraction comprising the hyrocarbons which were present in the demethanized rich solvent and not present in the purified rich solvent;

(d) separating the purified rich solvent from the primary fraction;

(e) regenerating the purified rich solvent to produce an acid gas comprising $H_2S$ and, expressed on a methane equivalent basis, less than about 5 molar % of hydrocarbon based on the acid gas and a regenerated solvent; and (f) recycling the regenerated solvent as the solvent for contacting the gaseous mixture.

2. A process according to claim 1 wherein the solvent contacting the gaseous mixture has a viscosity below 0.05 Pa.s.

3. A process according to claim 1 wherein the solvent contacting the gaseous mixture comprises at least one liquid organic absorbent selected from the group consisting of amides of the formula

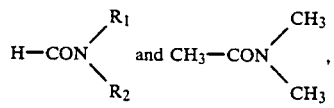

aldehydes of the formula

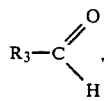

acetals of the formula

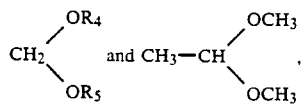

esters of the formula

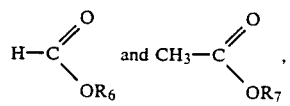

alkanols of from $C_1$ to $C_4$, diethers of the formula $CH_3O(C_2H_4O)_nCH_3$, diether alcohols of the formula $R_9O—C_2H_4—OH$, lactones of the formula

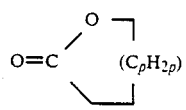

and propylene carbonate, wherein $R_1$ and $R_2$ may be identical or different, and designate a hydrogen atom or an alkyl radical of $C_1$ or $C_2$, $R_3$ is an alkyl radical of $C_3$ or $C_4$, $R_4$ and $R_5$ may be identical or different, and represent an alkyl radical of from $C_1$ to $C_3$, $R_6$ is an alkyl radical of from $C_2$ to $C_4$ or a$-(C_2H_4O)_n R_8$ radical wherein $R_8$ is an alkyl radical of $C_1$ or $C_2$ and n is 1 or 2, $R_7$ is an alkyl radical of $C_1$ or $C_2$ or $-(C_2H_4O)_n R_8$, $R_9$ is an alkyl radical of from $C_1$ to $C_4$ and p is an integer of from 2 to 4.

4. A process according to claim 1 wherein the temperature at which the gaseous mixture is contacted with the solvent is comprised between 0° C. and −45° C.

5. A process according to claim 1 wherein the gaseous mixture is contacted with the solvent in a contacting zone comprising at least one washing column which contains at least about 10 theoretical contacting stages.

6. A process according to claim 5, wherein the temperature in the at least one washing column is maintained within ±50° C. by indirect heat exchange (61) effected at one or more points of the column between the solvent in the column and a cooling fluid.

7. A process according to claim 1 wherein prior to contacting the solvent, the gaseous mixture is cooled to a temperature comprised between 0° C. and −30° C. to produce a liquid condensate phase (4) containing mainly hydrocarbons of $C_3$ and higher and $H_2S$ and a pre-treated gaseous phase (3), said pre-treated gaseous phase is then contacted with the solvent the solvent (8) is mixed with the condensate phase to form the rich solvent (9a) which is subjected to the demethanization.

8. A process according to claim 1 wherein prior to contacting the solvent, the gaseous mixture is cooled to a temperature comprised between 0° C. and −30° C. to produce a liquid condensate phase containng mainly hydrocarbons of $C_3$ and higher and $H_2S$ and a pre-treated gaseous mixture (3), said pre-treated gaseous mixture is contacted with the solvent and the rich solvent (8) and the condensates (4) from the cooling stage (2) are subjected to a separate demehtanization, the gaseous phases produced by the demethanization being recycled with the gaseous mixture (1) to the cooling stage (2), the solvent and the condensates from the separate demethanization treatments are joined to constitute the demethanized rich solvent (11).

9. A process according to claim 1 wherein the demethanization of the rich solvent and the condensates is carried out in two stages, comprising a first stage in which the liquid to be demethanized is subjected to a first expansion (29) at an intermediate pressure adequate to release a substantial fraction of the methane dissolved in the liquid and to produce a first gas rich in methane (34) and a pre-demethanized liquid (35), and a second stage in which the pre-demethanized liquid is subjected to a second expansion and then to a distillation (9) to produce a second gas rich in methane (32) and a demethanized liquid (11), the second gas rich in methane being compressed to the pressure of the first gas rich in methane, then admixed with the latter to comprise the gaseous phase (10) rich in methane.

10. A process of claim 9, wherein in the second stage of the demethanization the distillation (9) following the second expansion is effected by re-boiling, in at least two re-boiling zones (30a, 30b), arranged in series, by means of heat exchange with a fluid (31) comprising part of the gaseous mixture prior to contact with the solvent or prior to its cooling, or of part of the regenerated solvent.

11. A process according to claim 1 wherein the temperature, below the temperature of the demethanized rich solvent to which the demethanized rich solvent is cooled to separate it into said purified rich solvent and primary fraction, is comprised between −25° C. and −80° C.

12. A process according to claim 1 wherein the regeneration of the purified rich solvent includes a partial regeneration stage comprising an expansion (15) of the purified rich solvent to a pressure above 100 KPa followed by at least one partial vaporization (46,16) of said expanded solvent to produce at least one fraction (47,17) of acid gas and a semi-regenerated solvent (18) having a temperature at least equal to 0° C. and the pressure, below the pressure of the expanded solvent, is at least equal to 100 KPa, then a stage of total regeneration of the semi-regenerated solvent by distillation (20) to produce a fraction of acid gas (19) and regenerated solvent (21), said regenerated solvent being recycled (6) after cooling (22), to contact the gaseous mixture and the fractions of acid gas (47, 17, 19) are joined to form the current of acid gas (24) having a content of hydrocarbons, expressed in methane equivalent, less than 5% molar of the acid compounds.

13. A process of claim 12 wherein in the stage of partial regeneration of the purified rich solvent, the partial vaporization of the expanded solvent is effected by first carrying out a primary partial vaporization (46), of said solvent, to produce a primary fraction of acid gas (47) and a primary liquid phase (50) having a temperature below 0° C., then effecting a second partial vaporization (16) of the primary liquid phase to produce a secondary fraction of acid gas (17) and a secondary liquid phase (18) having a temperature at least equal to 0° C. and a pressure, below the pressur of the expanded solvent, at least equal to 100 KPa, said secondary liquid phase comprising the semi-regenerated solvent treated in the stage of total regeneration, the primary fraction of acid gas (47) being heated (49) to a temperature of at least 0° C., then joined to the secondary fraction (17) of acid gas and to the fraction of acid gas (19) resulting from the total regeneration of the semi-regenerated solvent to form the current of acid gas (24) having a content of hyrocarbons, expressed in methane equivalent, less than 5% molar of the acid compounds.

14. A process according to claim 12 wherein the total regeneration of the semi-regenerated solvent having been effected in a column (20) including a plurality of theoretical stages with the regenerated solvent being drawn off (21) at the bottom of the column, the semi-regenerated solvent is divided into two streams one of which is sent to the top plate of a distillation column and the other (52) feeds said column at the level of an intermediary theoretical stage after heating in counter-current heat exchange (52a) with the regenerated solvent from the column.

15. A process according to claim 1 wherein the purified rich solvent (11) is subjected, prior to regeneration, to a treatment of elimination of hydrocarbons, said treatment comprises putting into contact said solvent, in a primary liquid-liquid extraction zone (39) with an extraction agent comprising hdyrocarbons having a molecular weight higher than that of n-pentane to separate from said purified rich solvent a secondary liquid fraction (62) of hydrocarbons, joining said secondary fraction (62) to the primary fraction of heavy hydrocarbons (37), then heating (41) and distilling (42) the mixture thus obtained to produce the fraction of heavy hydrocarbons (13) containing at least 80% molar of the hydrocarbons of $C_3$ and higher present in the gaseous mixture and recovering the extraction agent (43) of which a major portion is recycled (40) to the primary liquid-liquid extraction zone (39) after cooling (44) to a temperature substantially equal to that reached during separation of the demethanized rich solvent into said purified rich solvent and primary fraction.

16. A process according to claim 1 wherein the treated gas is cooled (55) by at least 15° C. so as to produce a cooled treated gas (58) and a liquid fraction (57) which is subjected to the demethanization treatment in admixture with the rich solvent (9a).

17. A process according to claim 15 wherein the cooled treated gas is subjected to an additional contacting by a portion (45) of the extraction agent to produce a treated gas (7) of improved purity and a liquid fraction (61) which is recycled to distillation (41, 42) of a mixture of primary and secondary fractions of hydrocarbons.

18. A process according to claim 1 wherein prior to treatment the gaseous mixture is dried, debenzolated and contacted with anhydrous solvent to produce a dry gaseous mixture (26) having a content of aromatic hydrocarbons below 0.1% by weight and a hdyrocarbon fraction (27) containing the major portion of the aromatic hydrocarbons contained in the gaseous mixture and a liquid (28) comprising solvent containing water.

19. A process according to claim 1 wherein the gaseous mixture also comprises at least one compound selected from the group consisting of the inert gases, $H_2O$, $CO_2$, COS and mercaptans.

20. A process according to claim 19 wherein the gaseous mixture comprises at least one of COS and mercaptans, the solvent for $H_2S$ is also a solvent for said at least one of COS and mercaptans and the treated gas has a total partial pressure of sulphur containing compounds below about 260 Pa.

* * * * *

UNITED STATES PATENT AND TRADEMARK OFFICE
CERTIFICATE OF CORRECTION

PATENT NO. : 4,935,043
DATED : June 19, 1990
INVENTOR(S) : Blanc, et al

It is certified that error appears in the above-identified patent and that said Letters Patent is hereby corrected as shown below:

Column 1, line 35: change "one", first occurrence, to --on--

Column 2, line 49: change "F.the review" to --F. SCHAFFERT in the review--

Column 5, line 18: the second formula should read

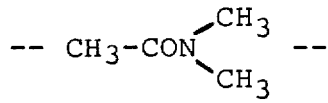

line 46: the formula should be written

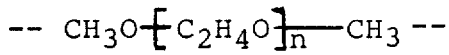

lines 61 and 63: the radical "$C_2H_4O_nR_8$" should be written -- $[C_2H_4O]_n\text{—}R_8$ -- line 62: change "an" to --n--

Column 7, line 3: change "revealed" to --recycled-- line 4: change "he" to --the-- line 10: change "in" to --it--

Column 9, line 28: change "demthanized" to --demethanized--

UNITED STATES PATENT AND TRADEMARK OFFICE
CERTIFICATE OF CORRECTION

PATENT NO.    : 4,935,043
DATED         : June 19, 1990
INVENTOR(S)   : Blanc, et al It is certified that error appears in the above-identified patent and that said Letters Patent is hereby corrected as shown below:

Column 9, line 35: delete "a"

line 47: change "dee-" to --de- --

Column 11, line 29: change "so" to --30-- line 34: change "dischared" to --discharged-- line 68: change "moledular" to --molecular--

Column 12, line 44: change "sovent" to --solvent--

Column 17, line 17: change "Kpa" to --KPa-- line 37: "73.76" in the table should read --73.78--

Column 19, line 28: change "$\alpha$" to --$\gamma$-- line 54: change "± 50°C" to --±5°C--

Column 20, line 38: change "th" to --the--

Column 21, Table : The value "60." given as hexane content at line 17 from the bottom should read --0.--

The value "0.08", second occurrence, given as butane content at line 3 from the bottom should read --0.06--

UNITED STATES PATENT AND TRADEMARK OFFICE
CERTIFICATE OF CORRECTION

PATENT NO. : 4,935,043

DATED : June 19, 1990

INVENTOR(S) : Blanc, et al

It is certified that error appears in the above-identified patent and that said Letters Patent is hereby corrected as shown below:

Column 23, line 59: change the formula "$R_9O-C_2H_4-OH$" to --$R_9O-C_2H_4O-C_2H_4-OH$--

Column 24, line 17: change "$\pm 50°C$" to --$\pm 5°C$-- line 33: change "containg" to --containing-- line 38: change "demehtanization" to --demethanization--

Column 25, line 33: change "pressur" to --pressure-- line 42: change "hyrocarbons" to --hydrocarbons--

Column 26, line 8: change "hdyrocarbons" to --hydrocarbons--

UNITED STATES PATENT AND TRADEMARK OFFICE
CERTIFICATE OF CORRECTION

PATENT NO. : 4,935,043

DATED : June 19, 1990

INVENTOR(S) : Blanc, et al

It is certified that error appears in the above-identified patent and that said Letters Patent is hereby corrected as shown below:

Column 26, line 39: change "hdyrocarbon" to --hydrocarbons--.

Signed and Sealed this

Fifth Day of May, 1992

*Attest:*

DOUGLAS B. COMER

*Attesting Officer*      *Acting Commissioner of Patents and Trademarks*